(12) United States Patent
Pelerin

(10) Patent No.: US 6,450,808 B1
(45) Date of Patent: Sep. 17, 2002

(54) DENTAL IMPRESSION TRAY

(75) Inventor: Joseph J. Pelerin, Clarkston, MI (US)

(73) Assignee: Advantage Dental Products, Inc., Lake Orion, MI (US)

(*) Notice: Subject to any disclaimer, the term of this patent is extended or adjusted under 35 U.S.C. 154(b) by 0 days.

(21) Appl. No.: 09/918,996

(22) Filed: Jul. 31, 2001

(51) Int. Cl.[7] ............................................... A61C 9/00
(52) U.S. Cl. ............................ 433/38; 433/37; 433/45; 433/46
(58) Field of Search ........................... 433/37, 38, 41, 433/42, 43, 44, 45, 46, 47

(56) References Cited

U.S. PATENT DOCUMENTS

| | | | | |
|---|---|---|---|---|
| 1,018,466 A | * | 2/1912 | Wilson | 433/47 |
| 4,204,323 A | * | 5/1980 | Neubert et al. | 433/38 |
| 4,619,610 A | * | 10/1986 | Pelerin | 433/41 |
| 4,689,010 A | * | 8/1987 | Wolfe | 433/38 |
| 5,513,985 A | * | 5/1996 | Robertson | 433/38 |
| 5,562,449 A | * | 10/1996 | Jacobs et al. | 433/48 |

* cited by examiner

*Primary Examiner*—John J. Wilson
(74) *Attorney, Agent, or Firm*—Gifford, Krass, Groh, Sprinkle, Anderson & Citkowski, P.C.

(57) ABSTRACT

A dental impression tray having a pair of spaced and outwardly flared sidewalls with a layer of material, such as gauze, netting, plastic or the like, or a rigid material, extending perpendicularly between the sidewalls. The sidewalls, furthermore, are dimensioned to extend substantially a one-half arch of a dental occlusion. The layer of material, however, extends outwardly from one end of the sidewalls so that the layer extends substantially a three-quarters of an arch of a dental occlusion. The dental impression tray is easily convertible between a one-half arch and a three-quarters arch of a dental occlusion by selectively removing the outwardly extending portion of the layer material. Additionally, a frame connects the sidewalls together while a notch in the frame enables the sidewalls to deflect upon occlusion and remain in a deflected position. Optionally, the sidewalls are eliminated.

4 Claims, 3 Drawing Sheets

U.S. Patent        Sep. 17, 2002        Sheet 1 of 3        US 6,450,808 B1
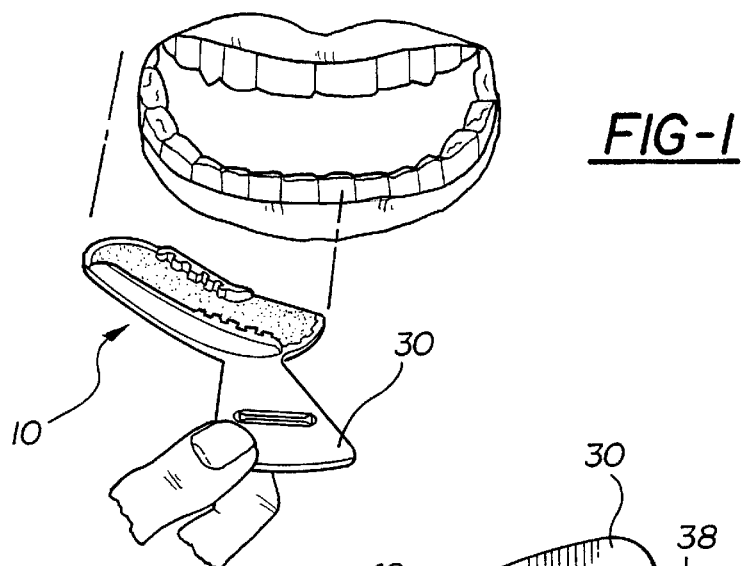
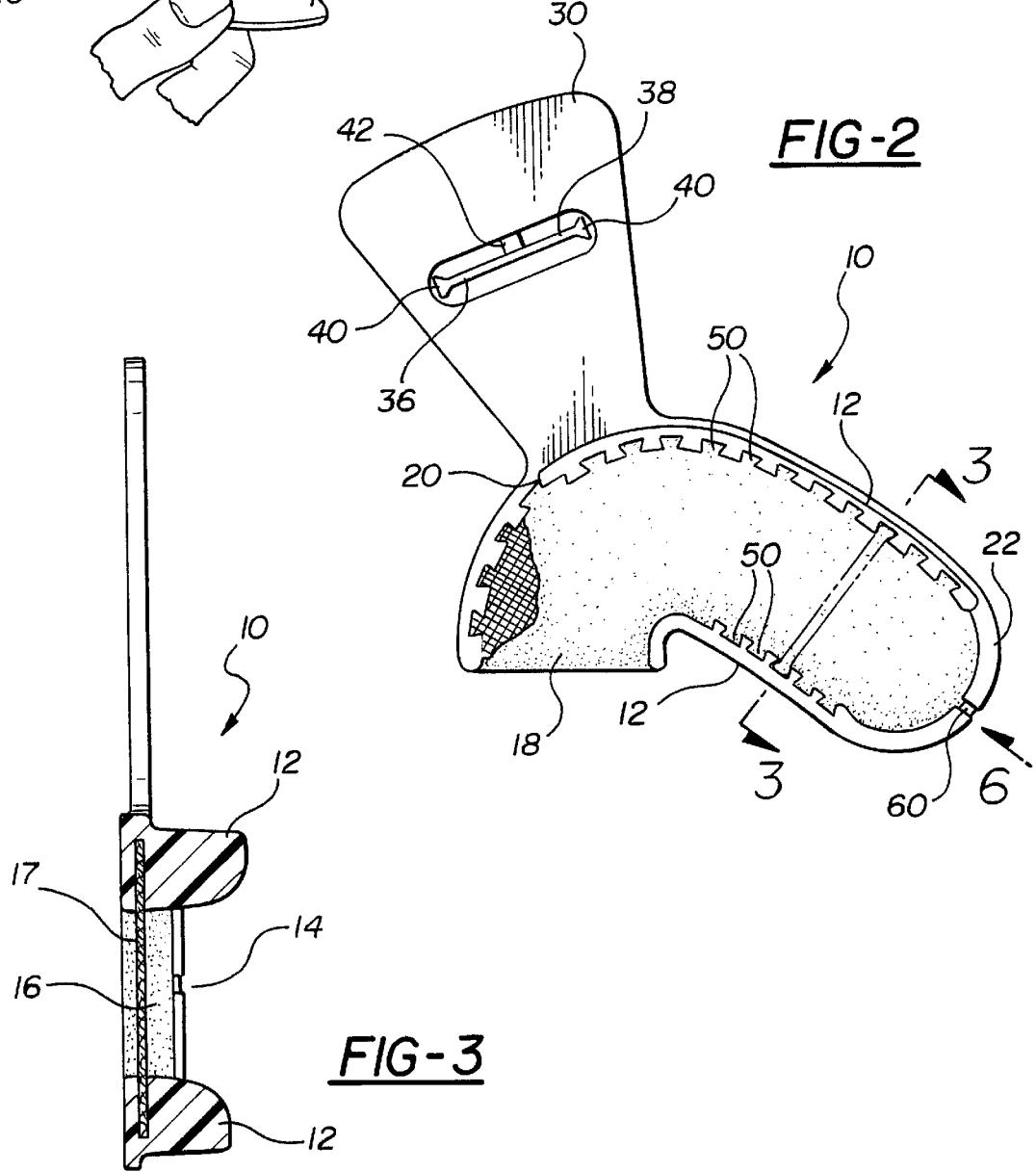

DENTAL IMPRESSION TRAY

BACKGROUND OF THE INVENTION

I. Field of the Invention

The present invention relates generally to a dental impression tray.

II. Description of Related Art

Dental impression trays, such as the dental impression tray disclosed in my earlier U.S. Pat. No. 4,619,610, are conventionally used to form dental impressions. These previously known dental impression trays typically comprise a pair of spaced sidewalls having a layer of rigid material extending between the sidewalls so that the sidewalls, together with the layer of rigid material, or optionally a gauze layer, netting, plastic or the like, form a channel.

In order to form the impression, the channel of the dental impression tray is filled with an impression material, such as silicon, and the patient occludes against the rigid material. Once the dental impression material has set, the impression tray together with the now set impression material is removed from the patient's mouth.

These previously known dental impression trays are typically manufactured in either one-half arch or three-quarters arch. For a one-half arch dental impression tray, the dental impression tray is dimensioned so that the tray extends along substantially one-half arch of the patient's bite. Conversely, a three-quarters quadrant tray is dimensioned so that the tray extends along a three-quarter arch of the patient's bite.

One disadvantage of these previously known dental impression trays, however, is that different trays were used in dependence upon whether a half arch or three-quarters arch dental impression was required. This necessarily increased the tooling for the dental impression trays and thus the overall cost of the dental impression tray.

A still further disadvantage of these previously known dental impression trays is that, upon occlusion, the rigid sidewalls of the dental impression trays occasionally bent outwardly during patient occlusion. Due to the rigidity of the tray, however, upon removal of the tray with the formed impression, the tray would "spring back" to its original shape so that the impression formed in the dental impression material did not precisely conform to the patient's bite. Consequently, the bridgework typically formed from the dental impression would oftentimes require time-consuming modification by the dentist in order for the bridgework to properly fit in the patient's mouth. Indeed, in some cases, such modification of the bridgework was not even possible so that it was necessary to take the dental impression and reform the dental bridgework.

SUMMARY OF THE PRESENT INVENTION

The present invention provides a dental impression tray which overcomes all of the above-mentioned disadvantages of the previously known dental impression trays.

In brief, the dental impression tray of the present invention comprises a pair of spaced sidewalls which are dimensioned to extend substantially a one-half arch of a dental occlusion. A layer of material extends perpendicularly between the sidewalls so that the layer together with the sidewalls forms a channel adapted to receive a dental impression material. The layer of material may be either rigid material or a flexible material, such as gauze.

Unlike the previously known dental impression trays, however, the layer of material extends outwardly from one end of the sidewalls such that the shape of the rigid material corresponds to a three-quarters arch of a dental occlusion. Consequently, when only a one-half arch impression of a dental occlusion is required, the outwardly extending portion of the layer material may be simply and readily removed by the dentist prior to taking the impression. Conversely, when a three-quarters arch impression of a dental occlusion is required, the dental impression material is placed not only between the sidewalls but as well as on the outwardly extending portion of the rigid material, gauze, netting, plastic or the like. This outwardly extending portion, furthermore, extends around the front of the patient's teeth and is easily visible and accessible by the dentist to ensure that a complete impression is made.

Preferably, the material extending between the sidewalls comprises polycaprolactone which becomes pliable above about 140° F. The polycaprolactone thus enables a bite trace to be easily formed in the rigid layer by simply heating the tray prior to taking the dental impression.

Alternatively, however, other materials, such as wax or even a flexible gauze, netting, mesh, plastic or the like, may be used.

In the preferred embodiment of the invention, a frame secured to the sidewalls extends around the end of the rigid layer opposite from its outwardly protruding portion. This frame, which preferably is of one-piece construction with the sidewalls, includes at least one reduced cross-sectional area segment intermediate its ends and optionally the frame may be used in lieu of the sidewalls. This reduced cross-sectional area segment minimizes any spring back between the dental impression tray sidewalls that may occur while taking the dental impression.

Additionally, one or more braces are optionally provided between the sidewalls to lock the sidewalls together against outward flexing. Preferably, a handle extends outwardly from one of the sidewalls and the brace is attached to the handle by a frangible link.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 1 is a perspective view illustrating a preferred embodiment of the present invention;

FIG. 2 is a top plan view illustrating a preferred embodiment of the present invention;

FIG. 3 is a sectional view taken substantially along line 3–3 in FIG. 2;

DETAILED DESCRIPTION OF PREFERRED EMBODIMENTS OF THE PRESENT INVENTION

Figure 4:
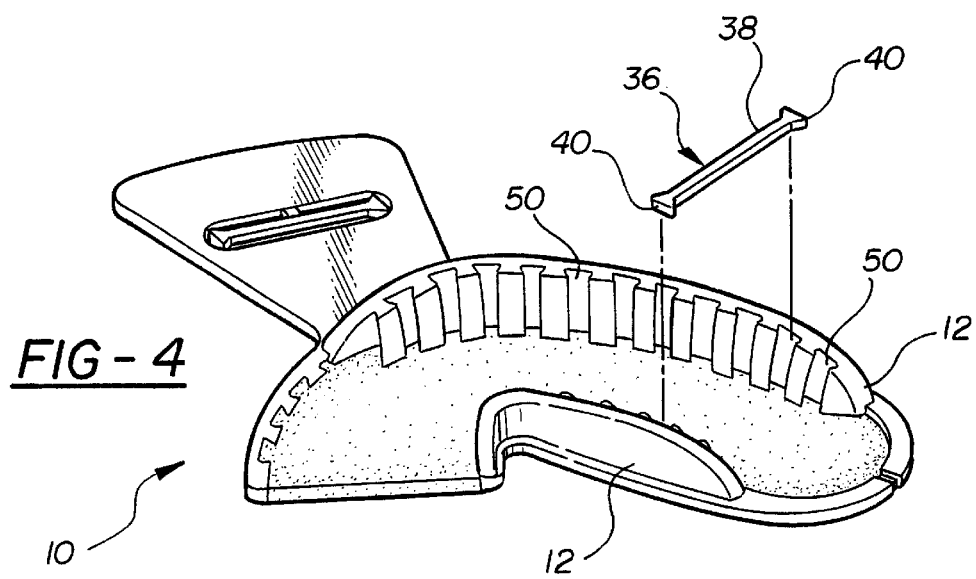
FIG. 4 is an exploded view illustrating one aspect of the preferred embodiment of the present invention.

With reference first to FIGS. 2 and 3, a preferred embodiment of the dental impression tray 10 of the present invention is there shown and comprises a pair of sidewalls 12 which are spaced apart and generally parallel to each other and form a channel 14 therebetween. The sidewalls 12, furthermore, are dimensioned to extend substantially a one-half arch of a dental occlusion, i.e. along one-half of a patient's bite. The sidewalls 12 also preferably flare outwardly from each other thereby avoiding contact with the patient's gums while minimizing the amount of dental impression material necessary to make an impression.

Still referring to FIGS. 2 and 3, a layer 16 of material extends between the sidewalls 12 and, together with the sidewalls 12, forms a generally U-shaped channel 14 therebetween. The layer of material 16, furthermore, preferably comprises polycaprolactone which becomes pliable above about 140° F. Other materials, however, such as wax, may alternatively be used. A gauze layer 17 (FIG. 3) is optionally embedded in the layer 16. The layer 16 may optionally be made of a flexible material, such as gauze, netting, mesh, plastic or the like.

As best shown in FIG. 1, since the sidewall 12 extends along only one-half arch, increased visibility is enhanced by the absent sidewall 12 along the remaining one-quarter arch of the tray 10.

Referring now particularly to FIG. 3, the layer 16 of material includes a portion 18 which extends outwardly from one end 20 of the outer sidewall 12. The rigid layer 16, furthermore, is dimensioned so that, together with its outwardly extending portion 18, the layer 16 extends around three-quarters arch of a patient's occlusion.

Referring now particularly to FIG. 2, a frame 22 extends around the end 24 opposite from the end 20 of the sidewalls 12 as well as around the outer side of the outwardly extending portion 18 of the layer 16 as shown at 26. This frame is generally coplanar with the rigid material 16 and adds some rigidity to the rigid layer 16.

Figure 7:
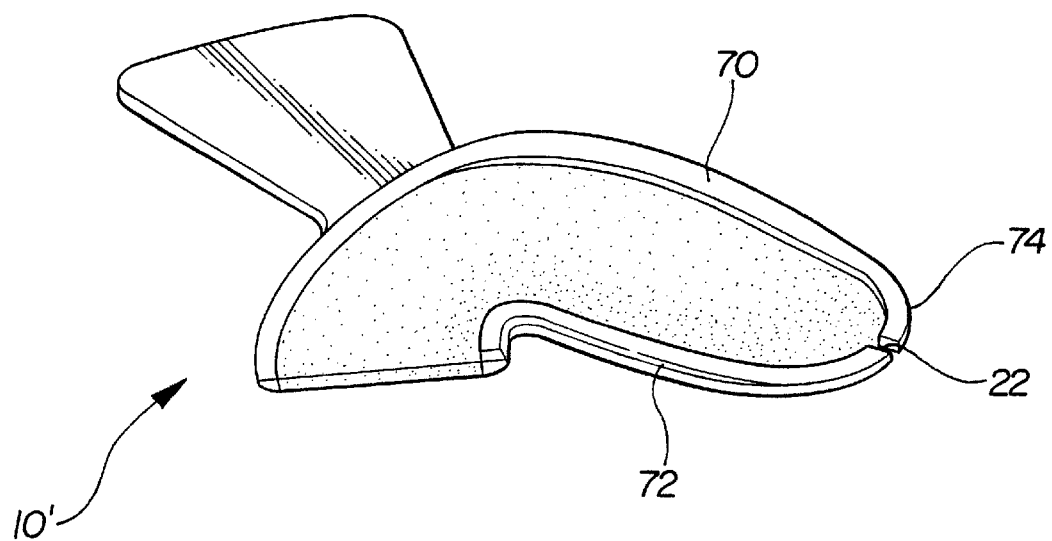
FIG. 7 is an elevational view illustrating a further preferred embodiment.

As shown in FIG. 7, the frame 22 may optionally be used with or without the sidewalls 12. When the sidewalls 12 are eliminated, the frame 22 and layer 16 is generally planar in shape. In this embodiment of the tray 10', the frame 22 is generally U-shaped having two spaced sides 70 and 72 and a bottom portion 74 connecting the sides 70 and 72 at at least one end.

In order to manipulate the impression tray 10, a handle 30 protrudes outwardly from the outer sidewall 12 and is preferably of a one-piece plastic construction with the sidewalls 12. Furthermore, a brace 36 having an elongated shank 38 and a cross bar 40 at each end is preferably connected to the handle 30 by a frangible link 42.

With reference now to FIGS. 2 and 4, a plurality of spaced T slots 50 are formed through each sidewall 12 so that the T slots 50 on one sidewall face the T slots 50 on the opposite sidewall 12. These T slots 50, furthermore, are dimensioned to receive the cross bars 40 of the brace 36. Thus, with the brace 36 positioned across the sidewalls 12, the brace 36 adds additional rigidity between the sidewalls 12.

Figure 5:
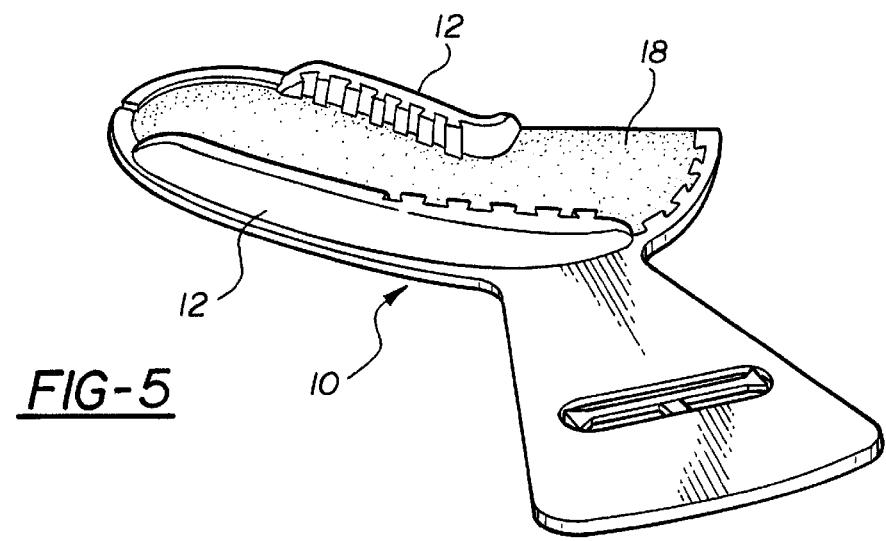
FIG. 5 is an exploded perspective view illustrating the conversion of the dental impression tray from a three-quarter quadrant to a one-half quadrant tray.

With reference now to FIG. 5, the dental impression tray 10 of the present invention can be utilized to take either a one-half or three-quarters arch impression of the dental occlusion. Specifically, if a one-half arch dental impression is desired, the outwardly protruding portion 18 of the layer 16 is removed from the tray 10 by merely cutting off the outwardly protruding portion 18 of the material 16 with scissors or the like. Thus, with the outwardly extending portion 18 of the layer 16 removed, a one-half arch dental impression tray is formed. The dental impression material, such as alginate or silicon, is then positioned within the channel 14 and the patient forms the impression by occluding against the layer 16. If desired, the layer 16 can also be used to record a bite trace. If the tray has only gauze netting or the like, impression material such as silicon is placed in both channels of the tray or both sides of the gauze netting or the like.

Conversely, if a three-quarters arch dental impression is desired, the dental impression material fills not only the channel between the sidewalls 12, but is also placed on top of the outwardly extending portion 18 of the layer 16 as shown in FIG. 1. The patient then occludes against the layer 16 to form the three-quarter arch dental impression. However, since the sidewall 12 does not extend around the outwardly protruding portion 18, visibility and accurate positioning of the tray 10 is maximized.

Figure 6:
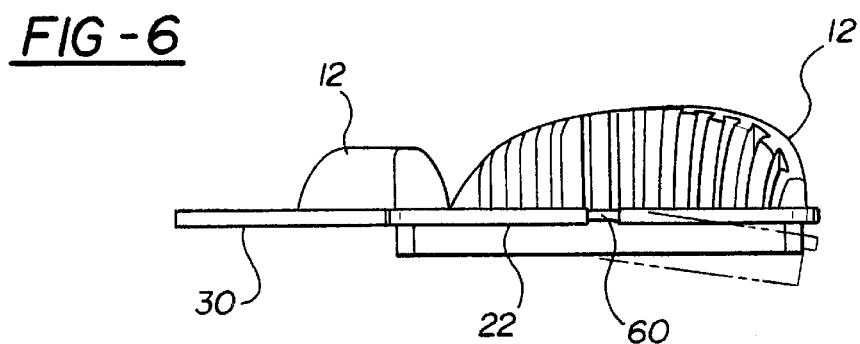
FIG. 6 is a view taken substantially along line 6–6 in FIG. 2.

With reference now particularly to FIGS. 2, 6 and 7, the frame 22 preferably includes at least one reduced cross-sectional area portion 60 at a midpoint along its length thus dividing the bottom portion of the frame 20 into two sections each of which extends for one-quarter of a quadrant of a circle. In the event that the sidewalls 12, or the frame 22 if the sidewalls 16 are eliminated, flex outwardly from each other during patient occlusion as shown in exaggeration in phantom line in FIG. 6, the frame 22 bends at its reduced diameter portion 60 thus reducing or altogether eliminating the amount of spring back of the sidewalls 18 after the dental impression material has set so that the sidewalls 12 remain in a deflected position.

From the foregoing, it can be seen that the present invention provides a simple and yet highly effective dental impression tray that is easily convertible from a three-quarter quadrant to a one-half quadrant tray. Having described my invention, however, many modifications thereto will become apparent to those skilled in the art to which it pertains without deviation from the spirit of the invention as defined by the scope of the appended claims.

I claim:

1. A dental impression tray comprising:

a U-shaped frame having two spaced apart side portions and an arcuate bottom portion connecting said side portions together at one end, said frame dimensioned to extend substantially a three-quarters arch of a dental occlusions, a layer of material extending perpendicularly between said frame side portions, said frame having a reduced cross-sectional area segment at a midpoint between the ends of said frame bottom portion such that said reduced cross-sectional area segment divides said frame bottom portion into two arcuate sections each of which extends for substantially a one-quarter quadrant of a circle, said reduced cross-sectional area segment being dimensioned to allow said side portions to flex relative to each other during a dental impression and remain in said deflected position.

2. The invention as defined in claim 1 wherein said layer is made of gauze.

3. The invention as defined in claim 1 wherein said layer is made of netting.

4. The invention as defined in claim 1 wherein said layer is made of plastic.

* * * * *